United States Patent
Bijlsma et al.

(10) Patent No.: US 6,686,341 B1
(45) Date of Patent: Feb. 3, 2004

(54) NUTRITIONAL COMPOSITIONS WHICH CONTAIN SLIGHTLY NEGATIVELY CHARGED, NON-DIGESTIBLE POLYSACCHARIDES AND USE THEREOF FOR REDUCING TRANSPORT THROUGH TIGHT JUNCTIONS

(75) Inventors: Pieter Brandt Bijlsma, Amsterdam (NL); Jacques Alphons Groot, Heiloo (NL); Johannes Wilhelmus Timmermans, Ede (NL); Jan Van Der Meulen, Dronten (NL); Amanda Johanna Kiliaan, Wageningen (NL)

(73) Assignee: N.V. Nutricia, Zoetermeer (NL)

( * ) Notice: Subject to any disclaimer, the term of this patent is extended or adjusted under 35 U.S.C. 154(b) by 0 days.

(21) Appl. No.: 09/937,395

(22) PCT Filed: Mar. 21, 2000

(86) PCT No.: PCT/NL00/00187
§ 371 (c)(1),
(2), (4) Date: Jan. 2, 2002

(87) PCT Pub. No.: WO00/57727
PCT Pub. Date: Oct. 5, 2000

(30) Foreign Application Priority Data

Mar. 26, 1999 (NL) .............................................. 1011680

(51) Int. Cl.[7] .................... A61K 31/715; A61K 31/721; A61K 31/736; A23L 1/308; C08B 37/00
(52) U.S. Cl. ........................ 514/54; 514/59; 536/123.1; 536/112; 536/117; 536/118; 536/120; 536/98
(58) Field of Search ................... 514/54, 59; 536/123.1, 536/112, 117, 118, 120, 98

(56) References Cited

U.S. PATENT DOCUMENTS 2,813,797 A    11/1957  Toulmin, Jr.
4,877,634 A *  10/1989  Pucci et al.
5,260,279 A    11/1993  Greenberg
5,616,570 A     4/1997  Lange, III et al.

FOREIGN PATENT DOCUMENTS

EP    0 153 013          8/1985
EP    0 648 495 A2       4/1995
JP    05244901 A2   *    9/1993

OTHER PUBLICATIONS

Mizuno et al. Foods containing Casein Phosphopeptides and polysaccharides (JP 05244901 A2) (abstract sent).*
Lanman et al., Life Sciences (1971), 10(14) (Pt. 2), 803–11 (abstract sent).*
Chang et al., Proc Soc Exp Biol Med 1988 Dec; 189 (3): 304–9 (abstract sent).*

* cited by examiner

*Primary Examiner*—Samuel Barts
*Assistant Examiner*—Michael C. Henry
(74) *Attorney, Agent, or Firm*—Young & Thompson

(57) ABSTRACT

A nutritional composition which contains slightly negatively charged non-digestible polysaccharides having a molecular weight of 8 kD to 40,000 kD, characterized in that the rise in the viscosity of the composition caused by the polysaccharides is less than 20 mpa·s. This nutritional composition is used to reduce the uptake of high molecular weight substances, allergens and microorganisms through the intestinal wall, more particularly to reduce transport of high molecular weight substances, allergens and microorganisms through the intestinal wall, ore particularly to reduce transport of high molecular weight substances, allergens and microorganisms through the tight junctions in the intestines. The nutritional compositions can be used to prevent or to treat allergies, allergic reactions, sepsis and inflammatory processes, such as those which can arise under emotional and physical stress, ischaemia, reperfusion damage during and after operations, following radiation treatment and/or chemotherapy of cancer patients and in the case of inflammatory intestinal diseases, diarrhoea and allergies.

10 Claims, 1 Drawing Sheet

Figure 1:
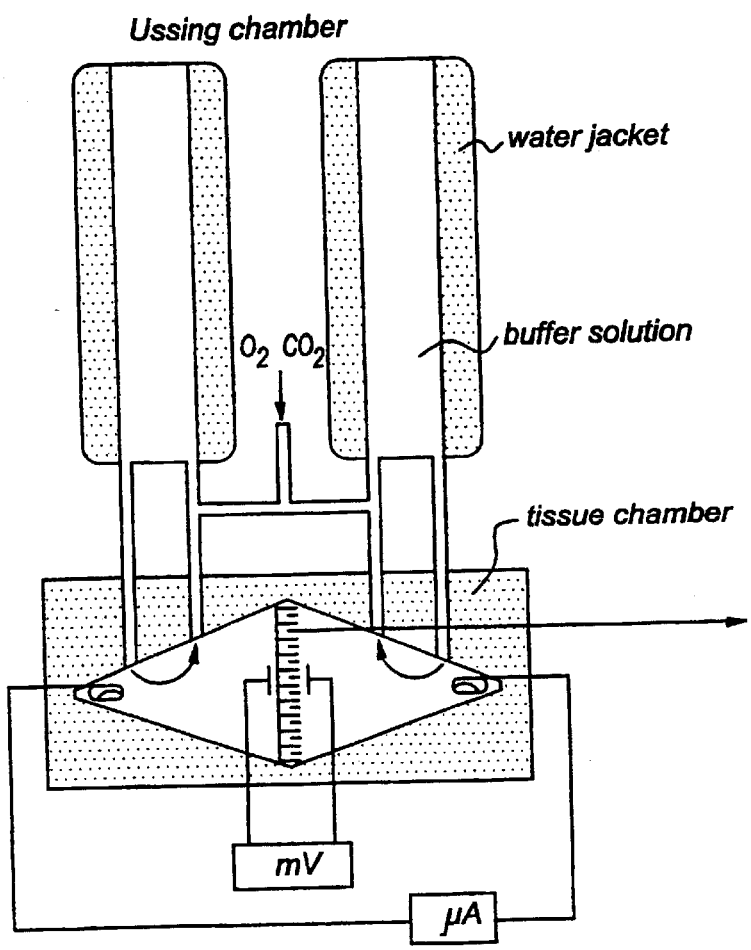

NUTRITIONAL COMPOSITIONS WHICH CONTAIN SLIGHTLY NEGATIVELY CHARGED, NON-DIGESTIBLE POLYSACCHARIDES AND USE THEREOF FOR REDUCING TRANSPORT THROUGH TIGHT JUNCTIONS

This is the National Phase Application of PCT/NL00/00187 filed, Mar. 21, 2000.

The present invention relates to nutritional compositions which contain certain classes of non-digestible polysaccharides. These compositions reduce the uptake of high molecular weight substances, allergens and microorganisms through the intestinal wall. In particular the present invention relates to reduction of the free transport of such substances through the tight junctions (TJs) of the intestines, without the transport of low molecular weight substances, such as nutrients, via the intestinal epithelium being impeded. The compositions can be used to prevent the increased permeability of the intestinal wall, due to various causes, and the penetration, resulting therefrom, of toxins, antigens and pathogenic microorganisms present in the lumen.

The structure and fraction of tight junctions is described, inter alia, in Ann. Rev. Physiol. 60, 121–160 (1998) and in Ballard T. S. et al., Annu.Rev.Nutr., 1995, 15:35–55. Tight junctions do not form a rigid barrier but play an important role in diffusion through the intestinal epithelium from lumen to bloodstream and vice versa.

The permeability of the tight junctions is highly regulated and can be disturbed by disease and certain toxins in the lumen. Regulation takes place from the nervous system, the hormonal system and the immune system. When tight junctions are opened substances having a high molecular weight, allergens and even microorganisms will pass through the tight junctions. The translocation of substances having a high molecular weight can, under certain conditions, give rise to sensitisation of the immune system and result in allergic reactions on a subsequent exposure. Translocation of pathogenic microorganisms makes a substantial call on the immune system and, inter alia in periods of reduced resistance, can make persons and animals ill. The same applies, for example, in the case of bacterial toxins which have been able to pass through the epithelial layer and have been able to reach the bloodstream.

The invention now relates to nutritional compositions which contain slightly negatively charged non-digestible polysaccharides having a molecular weight of 8 kD to 40,000 kD, characterised in that the rise in the viscosity of the composition caused by the polysaccharides is less than 20 mPa·s.

In particular the invention relates to the use of these compositions to reduce the uptake of high molecular weight substances, allergens and microorganisms through the intestinal wall.

More particularly the invention relates to the use of the abovementioned compositions to reduce transport of high molecular weight substances, allergens and microorganisms through the tight junctions in the intestines.

Some of the polysaccharides described above have already been described previously. U.S. Pat. No. 2,813,797 and U.S. Pat. No. 2,834,684 describe the use of carboxymethyldextran as a thickener, by which means the nutrient acquires certain desirable functional characteristics. This viscosity-raising effect is, as will be described below, undesirable in the case of the present invention.

Furthermore, in WO 97/41899 the thickening action of oxidised dextrans is used to make a wound dressing through which the active components are released in a controlled and slow manner to the tissue located under the dressing.

EP 0 772 446 describes the use of a combination of chitosan and dextran sulphate to prevent damaged tissue undesirably adhering to surrounding tissue. EP 0 759 760 discloses the stimulating action of the combination of chitosan and dextran sulphate on the healing of skin wounds.

In EP 0 754 460 it is described that sulphated acid mucopolysaccharides and dextran sulphate can be used for the treatment of diseases associated with inflammation, such as rheumatoid arthritis, ischaemia of the heart or brain, atopic dermatitis, infiltration following organ transplant.

In EP 0 737 072 it is described that sulphated polysaccharides such as dextran sulphate can prevent binding of bacteria to the wall of the respiratory system. WO 96/30027 discloses that sulphated polysaccharides such as carragheenan and dextran sulphate can be used to combat Rotavirus infections. EP 0 719 783 describes the use of non-digestible highly phosphorylated polysaccharides in nutrients to increase calcium absorption.

None of these documents describes the beneficial effect of slightly negatively charged polysaccharides as defined in claim 1 of this Application. More particularly, it is not described that these polysaccharides have an effect on the tight junctions in the intestines and in the event of disturbance of the permeability of the tight junctions are able to reduce the transport of high molecular weight substances, allergens and microorganisms through the tight junctions into the intestines.

In addition to the significant reduction in the transport of harmful substances and microorganisms, a significant advantage of the present invention is that the normal transport of useful substances (nutrients) such as glucose, amino acids, dipeptides or trace elements is substantially maintained.

According to the invention, non-digestible polysaccharides are understood to be polysaccharides which are not or are barely digested or converted by the human digestive enzymes under the conditions prevailing in the body. It must be pointed out that some of the non-digestible polysaccharides can be fermented by the microorganisms present in the intestines (colon, caecum and part of the ileum). Without wishing to be tied to any theory, it is, however, expected that the effect of the polysaccharides on the paracellular transport does not take place via the fermentation products.

The extent to which the polysaccharides are digested can be determined using the method as described in Minekus, M., Ph.D Thesis, University of Utrecht, 1998, Development and validation of a dynamic model of the gastrointestinal tract, Section 2. The polysaccharides according to the invention are less than 50% and preferably less than 30% digestible.

Preferably, the polysaccharides according to the invention contain groups which are negatively charged at pH 5.5–8, such as carboxyl, sulphate or phosphate, in a quantity of 1 negatively charged group per 3 to 10,000 saccharide units, preferably 1 negatively charged group per 10 to 10,000 saccharide units. Polysaccharides in which the negatively charged groups are carboxyl groups are most preferred.

These polysaccharides can be obtained via a synthesis route or by making use of naturally occurring polysaccharides.

Examples of modified polysaccharides are dextrans into which a negative group has been introduced, for example carboxydextran or carboxymethyldextran. Following or during hydrolysis of a high molecular weight dextran, one or more carboxyl groups can be introduced into the molecule by derivatisation. Derivatisation can, for example, take place by using the Kiliani-Fischer reaction or by carboxymethylation with, for example, chloroacetic acid or by oxidation of, for example, the reducing end of the molecule. Neutral naturally occurring polysaccharides can also be provided with one or more acid groups in this way. Examples of suitable naturally occurring polysaccharides are glucomannans; (galacto)mannans, such as guar gum, tara gum, carob gum and locust bean gum; curdlan; agar agar; arabans; (arabino)galactans, tamarind gum, pullulan and (arabino) xylans. Preferably the shortened forms or the hydrolysis products of these polysaccharides are used. Mixtures of modified polysaccharides can also be used.

Naturally occurring polysaccharides such as gum arabic, some carragheen preparations, chia gum, psyllium, gum tragacanth, ghatti gum, okra gum, some hemicellulose preparations, welan gum, rhamsan gum, gellan gum and certain pectins with a high degree of esterification are suitable as such, but much more preferentially in the hydrolysed form or shortened form obtained in some other way.

When polysaccharides contain too many negatively charged groups, such as, for example, alginates, some carragheen preparations, gellan gum, xanthan gum, karaya gum and many pectin preparations, the suitable quantity of negatively charged groups can be obtained by protecting a suitable fraction of these negatively charged groups, for example by esterification. By this means the specific interaction with the tight junctions can be increased.

Preferably, polysaccharides containing 1 carboxyl group per 10 to 10,000 saccharide units are used. A carboxydextran having a molecular weight of 20 to 2,000 kD and containing 1 carboxyl group per 10 to 10,000 saccharide units is particularly preferred.

The polysaccharides are preferably present in the preparation in a quantity such that the concentration of these polysaccharides in the intestines is 0.1 to 20 g/l, preferably 0.5 to 10 g/l, and most preferentially 1 to 6 g/l. The minimum quantity of the active substance is determined in that a significant decrease in the transport through the tight junctions is observed.

It is not necessary for the polysaccharides to be administered at that location where paracellular transport is disturbed. The presence of the active component at a location somewhere in the intestines between the stomach and the affected location is adequate.

Some of the polysaccharides used according to the invention have a viscosity-raising effect, which could prevent the absorption of nutritional components. The preparation must have a composition such that the normal transcellular transport is not impeded.

More particularly, the nutritional composition according to the invention has a viscosity of less than 100 mPa·s, preferably less than 40 and even more preferentially less than 30 mPa·s. For the present invention it is important, in particular, that the polysaccharides, irrespective of the other constituents of the composition, have only a slight viscosity-raising effect. The viscosity-raising effect of the active polysaccharides in the composition must be less than 20 and preferably less than 10 mPa.s and can be, for example, 3 mPa·s. The viscosity of the product is thus in the main caused by components in the product other than the polysaccharides.

The viscosity is determined by means of a Carri-med at a shear rate of 100 per second and at 20° C.

In the case of dry products the viscosity limits described above apply after reconstitution of the product.

In general, therefore, the type of polysaccharide (structure and molecular weight) and the concentration thereof will be so chosen that an optimum combination of effectiveness and viscosity is obtained. Not only molecular size, but also degree of branching and degree of loading determine activity, viscosity and/or fermentation behaviour.

The polysaccharides according to the invention prevent the free transport of high molecular weight substances, allergens and microorganisms through the tight junctions of the intestinal wall. In this context high molecular weight substances are understood to be the substances which under normal conditions are not able to pass through the tight junctions and for which a toxic or allergenic action can be assumed. These substances will in general have a molecular size of more than 4,000 Dalton. Antigens, substances which activate the immune system, are in general peptides, which may or may not be glycosidated, often with a molecular weight in excess of 10,000 Dalton. Allergens are antigens which give rise to an allergic reaction, which is usually mediated via immunoglobulin E.

In this context microorganisms are understood to be in particular microorganisms which occur in the intestinal lumen. Thus, for example, under certain conditions overgrowth of microorganisms in the small intestine can take place, as a result of which tight junctions are exposed to these microorganisms to an increased extent.

According to another aspect of the invention, foods or preparations are proposed which contain these slightly negatively charged, non-digestible polysaccharides. These foods can be:
complete foods;
food supplements;
health-promoting preparations; and
tube feeds.

The compositions according to the invention can be used to prevent or to treat allergies, allergic reactions, sepsis and inflammatory processes, such as those which can arise under emotional and physical stress, ischaemia, reperfusion damage during and after operations, following radiation treatment and/or chemotherapy of cancer patients and in the case of inflammatory intestinal diseases, diarrhoea and allergies.

The complete foods and food supplements described above can, in particular, be used for the treatment or prevention of inflammatory intestinal diseases, such as colitis ulcerosa, inflammatory bowel disease and Crohn's disease. Specific other constituents which can be incorporated in such foods and supplements are growth hormones, glutamines, n-3 LCPUFA's and the requisite contents of macro- and micro-ingredients.

Furthermore, the foods according to the invention can be used before and after operations. Specifically, ischaemia and reperfusion damage to the intestines often occurs during operations, as a result of which the tight junctions open. Introducing the polysaccharides according to the invention into the intestines before and after the operation could prevent uncontrolled paracellular transport. The administration of these polysaccharides can also be beneficial following chemotherapy.

In the case of diarrhoea a number of patho-morphological changes can also occur which are associated with increased permeability of the tight junctions. These changes can occur both in the case of travellers' diarrhoea and after diarrhoea following treatment with antibiotics and diarrhoea which follows after food poisoning. The complete foods and food supplements according to the invention can be used to counteract the adverse consequences of this increased permeability.

The tight junctions can also open during stress, both of a physical nature (for example endurance sports) and of an emotional nature, as a result of which bacterial translocation takes place. An example of emotional stress under which this takes place is the stress which occurs during the transport of pigs to the slaughterhouse. Contamination of the meat can occur as a result. Another example is the stress which occurs when weaning piglets. The polysaccharides can be administered before, during or after stress.

With the aid of the polysaccharides according to the invention it is also possible to prepare preparations which are suitable for patients who have a food allergy, such as an allergy to cow's milk or to gluten. The increase in the permeability as a result of exposure to the allergen can be prevented. These preparations are formulated such that the said allergens are not present therein.

Figure 2:
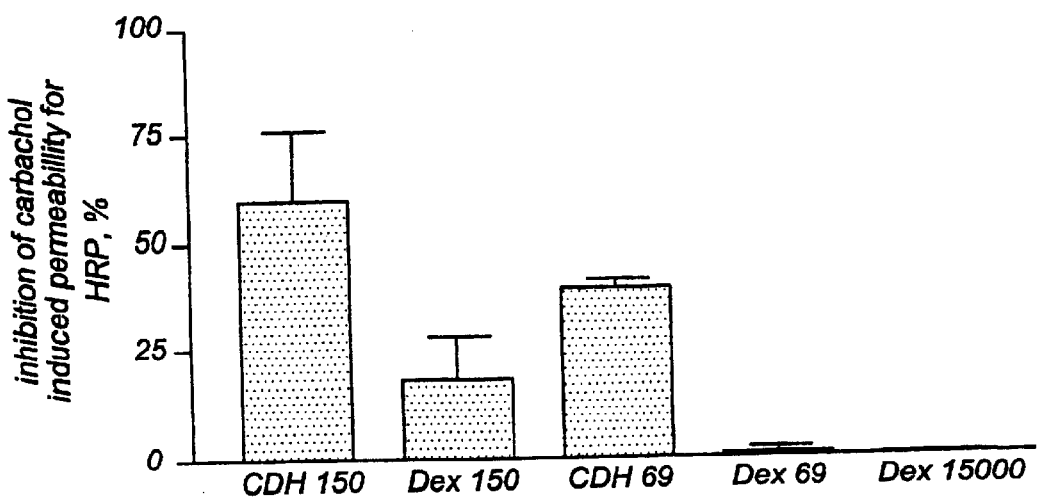

The invention is explained on the basis of the following examples and with reference to the appended figures, in which FIG. 1 shows the Ussing chamber used in the examples;

FIG. 2 shows a graphic by means of which the effect of the present invention is demonstrated; and FIG. 3 shows the test set-up used in the examples.

EXAMPLES

I. Methods for the Preparation of an Active Compound

Example 1

20 g slightly hydrolysed guar gum is dissolved in 300 ml dimethylformarnide. 50 g pyridine sulphur trioxide is added to this solution, after which the temperature is kept at 80 to 140° C. for 6 hours. The dimethylformamide is removed under reduced pressure, after which the product is dissolved in 300 ml water. After washing three times with 200 ml dichloromethane, the aqueous phase is dialysed and freeze-dried.

Example 2

Carboxydextran is obtained by dissolving 1.1 kg dextran (147 kD) in 2.3 l water and adding 17.4 g $NH_4Cl$ and 4.8 g KCN. After stirring for 40 hours at 55° C., 7 ml HCOOH is added and then $N_2$ gas is passed through vigorously for 3 hours. After adding a further 7 ml HCOOH, followed by freeze-drying, this yields dry cyanodextran. 1.1 kg of the latter is dissolved in 2 l water, after which 14.6 g $Na_2CO_3$ is added. After stirring for 136 hours at 60° C. whilst passing $N_2$ gas through vigorously and then freeze-drying, the desired carboxydextran is obtained.

Example 3

Carboxymethyldextran having a molecular weight of 147,000 Dalton is obtained by dissolving 100 g dextran (147 kD) in 500 ml water and adding 40 g NaOH and 12 g chloroacetic acid to this solution. The mixture is stirred for 2 hours at 60° C., after which ⅚ of the mixture is worked up. After precipitating three times from water by means of ethanol, the product is dissolved in water, dialysed and freeze-dried.

Example 4

Guar phosphate is obtained by dissolving 20 g slightly hydrolysed guar gum in 500 ml water together with 20 g $NaH_2PO_4$ and 30 g $Na_2HPO_4$. A phosphorilated guar with a Ts<0.1 is obtained by this means. This is then dried at 60° C., after which it is kept at 140° C. for 2 hours. It is then dialysed and then dried.

II Examples of Products

Examples of compositions of various types of products in which the active component is carboxydextran are given below. It is in line with the invention that the other polysaccharides described in this application, as well as mixtures thereof, can also be used.

The various types of product can be complete enteral food, for use by the patient him/herself or for use as a tube feed. The product can be either in liquid form or in powder form which is ready for use after dissolving. The active components can also be used as an ingredient in another food (for example bread) or in food supplements, such as a bar, a dairy product, such as yoghurt, or a powder in the form of a sachet.

Example 5

Ready-to-feed, liquid, complete food for use before or after operations. Per 100 ml, the product has the following composition:

| | |
|---|---|
| Protein: | 7.0 g |
| Fat: | 4.0 g |
| Carbohydrates: | 21 g |
| Carboxydextran according to Example 2: | 0.2 g |

Minerals are added in an amount of 1/15 of the recommended daily allowance (=RDA) per 100 ml of the product. Trace elements and vitamins are added in somewhat higher amounts, i.e. 2/15 RDA. The product is formulated such that 1,500 ml has to be consumed by the patient.

Example 6

Complete food for administering by tube to persons suffering from inflammatory bowel disease. The product contains the following, per 100 ml:

Protein based on casein: 7.0 g

Fat based on vegetable oils and 10% fish oil and 20% MCT; the linoleic acid content is 20% and the alpha-linolenic acid content 4.5%

Premixes with the customary forms of trace elements, vitamins and minerals Na, K, Ca, Mg, P, Zn, Fe, Mn, Cu, Vit. B1, B2, niacin, A, D, K, B6, B12, pantothenic acid, folic acid.

Carboxydextran according to Example 2: 0.6 g

Example 7

Food supplement for patients suffering from food intolerance or allergy.

Yoghurt based on soya milk. The yoghurt contains the following per 100 ml:

Protein 4.0 g, fat 3.9 g, carbohydrates 12.3 g and 0.1 RDA of vitamins and trace elements.

Na=80; K=135; Cl=125; Ca=50; P=50; Mg=20 mg

Carboxydextran according to Example 2: 0.5 g

Example 8

Energy Drink for Athletes.

The liquid contains the following per 100 ml

| | |
|---|---|
| Carbohydrates: | 7.0 g |
| Glucose: | 0.2 g |
| Fructose: | 1.8 g |
| Lactose: | 0.4 g |
| Saccharose | 1.7 g |
| Polysaccharides: | 2.5 g |
| Organic acids: | 0.4 g |
| Minerals: | |
| Na: | 37 mg |
| K: | 17 mg |
| Cl: | 58 mg |
| Ca | 8 mg |
| Mg: | 1 mg |
| Vitamin C: | 15 mg |

Carboxydextran according to Example 2: 0.1 g

Example 9

Premix for use in pig or piglet feed. A/Premix consisting of 90% maize flour and 10% 150 kD carboxydextran. B/Premix consisting of a suitable premix of vitamins, trace elements and minerals and 10% carboxydextran prepared in accordance with Example 2. Premix A, B or mixtures thereof can be used in the preparation of pig feeds. These can be special feeds for use when pigs are loaded for transport or have to be allocated different positions in the sty or if they have a period of reduced resistance.

The premixes can also be used in a piglet feed for use after weaning, as an additive to or instead of the premixes which are already known for use in piglet feed.

III Effect on Transport via the Tight Junctions of the Intestines

Use was made of a model set-up to determine the effect of the polysaccharides used. A rat is brought under narcosis. The stomach wall is then opened and a section of the ileum is tied off. The intestinal tissue is removed and muscle layers stripped from it. The preparation thus obtained is then stretched between two compartments through which oxygenated solutions are flowing (FIG. 1). The preparation was treated either with buffer (control or zero value) or carbachol in buffer to open the tight junctions (100% permeability) or with the combination of carbachol and a certain concentration of polysaccharide in buffer. As a measure of the permeability the transport of HRP (horseradish peroxidase) over the preparation is measured in accordance with known methods.

It is shown in FIG. 2 that carboxydextrans lower the rise in the permeability of the intestines as a consequence of carbachol, in contrast to neutral dextrans of comparable molecular weight.

Suction biopsies of the duodenum were taken from two children suffering from microvillus inclusion disease. In the Ussing chamber these preparations showed a permeability for HRP that was four times higher than the normal value. After adding 4.2 g 70 kD carboxydextran to the luminal compartnent in the Ussing chamber the permeability was reduced to the normal level. No further HRP could be detected in the paracellular spaces or tight junctions by means of electron microscopy.

What is claimed is:

1. A nutritional composition, comprising: non-digestible polysaccharides, said polysaccharides contain groups which are negatively charged at pH 5.5–8 and in a quantity of 1 negatively charged group per 3 to 10,000 saccharide units, said polysaccharides have a molecular weight of 8 kD to 40,000 kD, and the rise in the viscosity of the composition caused by the polysaccharides is less than 20 mPa·s as determined by a Carri-med at a shear rate of 100 per second at 20° C.

2. Nutritional composition according to claim 1, wherein the polysaccharides contain 1 negatively charged group per 10 to 10,000 saccharide units.

3. Nutritional composition according to claim 1, wherein the negatively charged groups are carboxyl, sulphate or phosphate groups.

4. Nutritional composition according to claim 1, wherein the polysaccharides have been obtained by introduction of an acid group into dextrans, slightly hydrolysed, neutral galactomannans, neutral glucomannans or arabinoxylans.

5. Nutritional composition according to claim 1, wherein the polysaccharides are carboxydextrans having a molecular weight of 20 to 2,000 kD and containing 1 carboxyl group per 10 to 10,000 saccharide units.

6. Nutritional composition according to claim 1, wherein said composition is in the form of a complete food.

7. Nutritional composition according to claim 1, wherein said composition is in the form of a food supplement.

8. Nutritional composition according to claim 3, wherein the negatively charged groups are carboxyl groups.

9. Nutritional composition according to claim 1, wherein the polysaccharides have a molecular weight of 20 to 2,000 kD.

10. Nutritional composition according to claim 1, wherein said polysaccharide contains 1 carboxyl group per 10 to 10,000 saccharide units.

* * * * *